Figure 1:
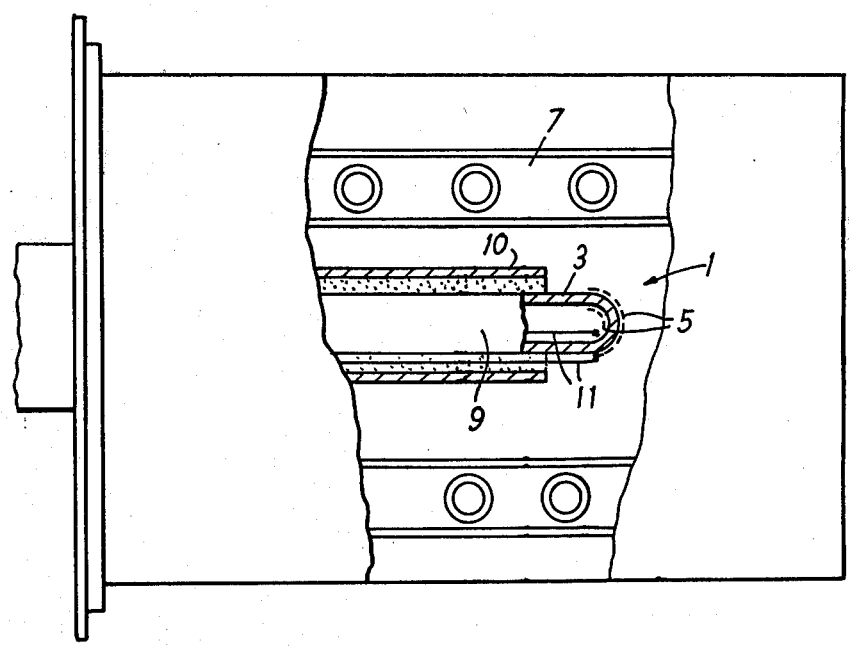

United States Patent [19]

Record

[11] 4,037,773
[45] July 26, 1977

[54] BONDING OF METALS TO SOLID ELECTROLYTES

[75] Inventor: Robert George Hamilton Record, Luton, England

[73] Assignee: George Kent Limited, Luton, England

[21] Appl. No.: 638,090

[22] Filed: Dec. 5, 1975

[30] Foreign Application Priority Data

Dec. 9, 1974 United Kingdom ............... 53229/74

[51] Int. Cl.² ............................................. B44D 1/50
[52] U.S. Cl. .................................................... 228/122
[58] Field of Search ............... 228/178, 245, 246, 248, 228/220, 261, 253, 254, 903, 122, 123, 208; 427/191

[56] References Cited
U.S. PATENT DOCUMENTS

| 3,029,559 | 4/1962 | Treptow | 228/122 X |
| 3,598,635 | 8/1971 | Sagona | 427/191 X |
| 3,672,881 | 6/1972 | Sowko | 228/903 X |

Primary Examiner—Al Lawrence Smith
Assistant Examiner—Robert C. Watson
Attorney, Agent, or Firm—Browdy and Neimark

[57] ABSTRACT

A method of bonding a metal to a solid electrolyte, suitably for making an electrolytic cell for measuring the oxygen content of gases. A layer of the metal is first applied to a surface of the material and the material is then heated in an atmosphere consisting or consisting substantially of hydrogen at a temperature and for a time sufficient to effect bonding of the metal to the material.

12 Claims, 2 Drawing Figures

U.S. Patent

July 26, 1977

4,037,773

BONDING OF METALS TO SOLID ELECTROLYTES

This invention relates to the bonding of metals to solid electrolytic material.

Probes have been proposed for determining the oxygen content of flue gases which rely for their operation on the ability of certain ceramic materials, such as zirconia, to act as solid electrolytes when heated to high temperatures. The materials are insulators at low temperatures but become conductive when heated to high temperatures. Their ability to do so arises from the presence of vacant oxygen sites in the crystal lattice. If the pressure of oxygen in the gas on one side of the material is equal to the pressure of oxygen in the gas on the other side an equilibrium is established at high temperatures between the oxygen in the lattice and the external oxygen. However, if there is a difference between the pressure of oxygen on one side and that on the other side there is a general movement of oxygen ions through the lattice, oxygen being absorbed from the gas with the higher pressure of oxygen and being released into the gas with the lower pressure. The movement of oxygen ions generates an e.m.f. which is detected as a potential difference between electrodes of a noble metal which are provided on respective opposite sides of the material. The magnitude of the potential difference is representative of the difference between the pressures of oxygen in the two gases.

In making the probes referred to above it is desirable to provide a maximum area of contact between each electrode and the electrolytic material and between each electrode and the oxygen in the surrounding atmosphere. At the same time, the electrodes should have a porous structure, which allows ready access of oxygen to the electrolytic material, and they should be firmly bonded to the electrolyte.

The present invention includes a method of bonding a metal to a solid electrolytic material comprising applying a layer of the metal to a surface of the material, and then heating the material in an atmosphere consisting or consisting substantially of hydrogen at a temperature and for a time sufficient to effect bonding of the metal to the material.

The layer of metal may be applied by applying a paste comprising particles of the said metal suspended in a solvent and a binder to the surface, and then drying and heating to evaporate the solvent and binder.

The solid electrolyte material may be zirconia or zirconia stabilized with lime or with yttria. In this case the metal is preferably platinum or an alloy of gold and palladium.

Preferably, bonding is effected by heating in a hydrogen atmosphere for 1 to 3 hours at a temperature within the range from 1,050° to 1,550° C.

Figure 2:
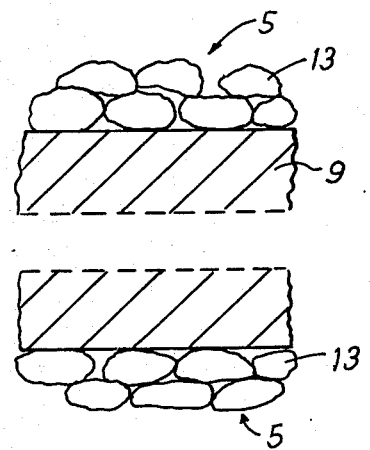

The invention will now be described, by way of example, with reference to the accompanying drawings, in which:

FIG. 1 is a side elevation, partly in section, of an electrolytic cell having electrodes bonded to solid electrolytic material by a method according to the invention; and FIG. 2 is an enlarged sectional view of part of the cell of FIG. 1.

One method according to the invention is used in making a probe for determining the oxygen content of low temperature flue gases. Referring to FIG. 1 of the drawings, the probe includes an electrolytic cell 1 made up of a solid electrolyte 3 contacted on opposite sides thereof by metal electrodes 5. A furnace 7 is provided for heating the cell 1 to a temperature at which the electrolyte 3 has become conductive.

In the present probe the electroltye 3 is zirconia stabilized with lime and is formed as a short tube 9 which is open at one end and closed at the other. The zirconia tube 9 is mounted in a stainless steel supporting tube 10, which also supports the furnace 7. The electrodes 5 are provided at or near the closed end of the zirconia tube 9 and are connected to external measuring circuits (not shown) via electrical leads 11. A reference gas is supplied to the interior of the zirconia tube 9.

Referring to FIG. 2, each electrode 5 in the present probe is formed by applying a paste made up of a suspension of platinum particles 13 in organic solvents and binders to the inner and outer surfaces of the closed end of the zirconia tube 9. The paste is dried in air and then heated in air to a temperature of 1300° C, in order to evaporate the solvents and binders and to sinter the platinum.

After this drying and heating the zirconia is placed in a furnace charged with hydrogen and heated to a temperature of 1300° C. The zirconia is maintained at temperature for one hour and then allowed to cool to room temperature.

It is found that platinum electrodes 5 formed by this method have a large area of contact with the zirconia tube 9 and adhere strongly thereto. In use, the electrodes 5 provide a reliable measure of the e.m.f. developed in the material. At the same time, the platinum is porous and allows ready access of oxygen in the surrounding atmosphere to the zirconia.

It is found that bonding can be effected at a lower temperature if the time for which the temperature is maintained is increased. Thus, a bonding temperature of 1,050° C may be satisfactory if heating is continued for approximately three hours.

Instead of applying the platinum particles 13 in the form of a paste it is possible to use a flame spraying or sputtering process. In this case the need for an initial heat treatment to evaporate organic solvents and binders is avoided.

As an alternative to platinum, other noble metals such as an alloy of gold and palladium can be used. The present method can also be used for bonding base metals and alloys to solid electrolytes.

I claim:

1. A method of bonding a metal to a solid electrolyte material, suitably for making an electrolytic cell for measuring the oxygen content of gases, comprising:
   applying a layer of the metal to a surface of the material; and then
   heating the material in an atmosphere consisting or consisting substantially of hydrogen at a temperature and for a time sufficient to effect bonding of the metal to the material.

2. A method as claimed in claim 1, wherein the layer of metal is applied by applying a paste comprising particles of the said metal suspended in a solvent and a binder to the surface, and then drying and heating to evaporate the solvent and binder.

3. A method as claimed in claim 1, wherein the layer of metal is applied by flame spraying or sputtering.

4. A method as claimed in claim 1, wherein bonding is effected by heating in a hydrogen atmosphere for 1 to 3 hours at a temperature within the range from 1,050° to 1,550° C.

5. A method as claimed in claim 1, wherein the solid electrolyte is zirconia or zirconia stabilized with lime or with yttria.

6. A method as claimed in claim 1, wherein the metal is platinum or an alloy of gold and platinum.

7. A solid electrolytic material having a metal bonded thereto by the method as claimed in claim 1.

8. A method in accordance with claim 1, wherein said solid electrolytic material is one in which ionic conduction may be effected by a movement of oxygen ions at high temperature.

9. A method in accordance with claim 1, wherein the metal is an alloy of gold and platinum or an alloy of gold and palladium.

10. In an electrolytic cell for measuring the oxygen content of gases, including a base of solid electrolytic material having electrodes of metal bonded to each side thereof, the improvement wherein the bonding is accomplished in accordance with the method of claim 1.

11. A method as claimed in claim 1 wherein the metal is a noble metal.

12. A method as claimed in claim 1, wherein the metal is applied in a manner such that, after said heating step, the metal is sufficiently porous when in use to allow ready access of oxygen in the surrounding atmosphere to the material.

* * * * *